United States Patent [19]

Martinis et al.

[11] Patent Number: 5,656,470

[45] Date of Patent: Aug. 12, 1997

[54] RECOMBINANT MYCOBACTERIAL SERYL-TRNA SYNTHETASE GENES, TESTER STRAINS AND ASSAYS

[75] Inventors: Susan A. Martinis, Newton; Jiansu Zhang; Paul R. Schimmel, both of Cambridge, all of Mass.

[73] Assignee: Cubist Pharmaceuticals, Inc., Cambridge, Mass.

[21] Appl. No.: 305,172

[22] Filed: Sep. 13, 1994

[51] Int. Cl.$^6$ .............................. C12N 9/00; C12N 1/20; C12N 15/00; C07H 21/04

[52] U.S. Cl. .................. 435/183; 435/252.3; 435/320.1; 536/23.2

[58] Field of Search .......................... 435/252.3, 320.1, 435/183; 536/23.2

[56] References Cited

U.S. PATENT DOCUMENTS

| | | | |
|---|---|---|---|
| 4,713,337 | 12/1987 | Jasin et al. | 435/172.3 |
| 4,952,501 | 8/1990 | Jasin et al. | 435/69.2 |
| 4,963,487 | 10/1990 | Schimmel et al. | 435/172.3 |

OTHER PUBLICATIONS

Laske, R., et al., "Untersuchungen zum Wirkmechanismus antimykobakterieller Benzylamine," *Arch. Pharm.* (Weinheim), 322:297–299 (1989).

Gopinathan, K. P., "Molecular Biology of Mycobacteria and Mycobacteriophages," *J. Indian Inst. Sci.*, 73:31–45 (1993).

Deobagkar, D. N. and Gopinathan, K. P., "Studies on Transfer RNA from Mycobacteria," *Can. J. Microbiol.*, 24:693–702 (1978).

Edwards, H., et al., "An *E. coli* Aminoacyl–tRNA Synthetase Can Substitute for Yeast Mitochondrial Enzyme Function In Vivo," *Cell* 51:643–649, Nov. 20, 1987.

Racher, K.I., et al., "Expression and Characterization of a Recombinant Yeast Isoleucyl–tRNA Synthetase," *The Journal of Biological Chemistry* 266(26):17158–17164, Sep. 15, 1991.

von der Haar, F. et al, "Target Directed Drug Synthesis: The Aminoacyl–tRNA Synthetases as Possible Targets," *Angew. Chem. Int. Ed. Engl.*, 20(3):217–223 (1981).

Chalker, A.F., et al., "Analysis and Toxic Overexpression in *Escherichia coli* of a Staphylococcal Gene Encoding Isoleucyl–tRNA Synthetase," *Gene*, 141:103–108 (1994).

Hughes, J. and Mellows, G., "Interaction of Pseudomonic Acid A with *Escherichia coli* B Isoleucyl–tRNA Synthetase," *Biochem J.*, 191:209–219 (1980).

Weygand–Duraševič, et al., "Yeast Seryl–tRNA Synthetase Expressed in *Escherichia coli* Recognizes Bacterial Serine–Specific tRNAS in vivo," *Eur. J. Biochem.* 214:869–877 (1993).

Walter, R. D. and Kuhlow, F., "Parasite–Specific Interaction of N–[4–(4' Nitroanilino)–Phenyl]– S–(β– Carboxyethyl)–Dithiocarbamic Acid–Ester with Arginyl–tRNA–Synthetase from *Dirofilaria immitis*," *Trop. Med. Parasit.* 36:230–232 (1985).

Meinnel, T., et al., "Aminoacyl–tRNA Synthetases: Occurrence, Structure, and Function." In *tRNA: Structure, Biosynthesis, and Function*, Söll, D. and RajBhandary, U., eds. (Washington, DC: American Society for Microbiology), pp. 251–300 (1995).

Härtlein, M., et al., "Cloning and Characterization of the Gene for *Escherichia coli* Seryl–tRNA Synthetase," *Nucleic Acids Research*, 15(3):1005–1017 (1987).

Fujinaga, M., et al., "Refined Crystal Structure of the Seryl–tRNA Synthetase from *Thermus thermophilus* at 2.5 Å Resolution," *J. Mol. Biol.* 234:222–233 (1993).

Lunel, C., et al., "A Seryl–tRNA Synthetase Gene is Coamplified with the Adenylate Deaminase 2 Gene in Coformycin Resistant Chinese Hamster Fibroblasts, " *Nucleic Acids Research*, 20(10):2597 (1992).

Weygand–Duraševič, I., et al., "Cloning and Characterization of the Gene Coding for Cytoplasmic Seryl–tRNA Synthetase from *Saccharomyces cerevisiae*," *Nucleic Acids Research*, 15(5):1887–1904 (1987).

Jasin, M. and Schimmel, P., "Deletion of an Essential Gene in *Escherichia coli* by Site–Specific Recombination with Linear DNA Fragments," *J. Bacteriol.*, 159(2):783–786 (1984).

Low, B., et al., "Isolation and Partial Characterization of Temperature–Sensitive *Escherichia coli* Mutants with Altered Leucyl– and Seryl– Transfer Ribonucleic Acid Synthetases," *Journal of Bacteriology*, 108(2):742–750 (1971).

Clarke, S. J., et al., "Isolation and Characterization of a Regulatory Mutant of an Aminoacyl–Transfer Ribonucleic Acid Synthetase in *Eschericia coli* K–12," *Journal of Bacteriology*, 113(3):1096–1103 (1973).

(List continued on next page.)

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

Isolated and/or recombinant nucleic acids encoding mycobacterial seryl–tRNA synthetase have been characterized. Recombinant DNA constructs and vectors having a sequence which encodes mycobacterial seryl–tRNA synthetase have been made, and can be used for the construction of tester strains as well as for the production of isolated and/or recombinant seryl–tRNA synthetases. These enzymes or portions thereof are useful in the biochemical separation of serine and quantification of serine or ATP, and for producing antibodies useful in the purification and study of the enzyme, for example. Host cells and methods useful for producing recombinant mycobacterial seryl–tRNA synthetases are described, as are tester strains, which are cells engineered to rely on the function of the tRNA synthetase encoded by an introduced cloned gene. Tester strains can be used to identify inhibitors of the essential tRNA synthetase enzyme encoded by the introduced cloned gene, and thus provide a means to assess the antimicrobial effect and specificity of the inhibitor without employing slow-growing, pathogenic strains of mycobacteria, such as *Mycobacterium tuberculosis*.

19 Claims, No Drawings

OTHER PUBLICATIONS

Miseta, A., et al., "Mammalian Seryl-tRNA Synthetase Associates with mRNA in Vivo and Has Homology to Elongation Factor 1α," *The Journal of Biological Chemistry*, 266(29):19158–19161 (1991).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology*, 10(4):1633–1641 (1990).

Hughes, J. and Mellows, G., "Inhibition of Isoleucyl–Transfer Ribonucleic Acid Synthetase in *Escherichia coli* by Pseudomonic Acid," *Biochem. J.*, 176:305–318 (1978).

Cusack et al. (1990) Nature 347: 249–255.

Kumazawa et al. (1991) J. biochem. 109(3): 421–427.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: modified_base
        ( B ) LOCATION: 6
        ( D ) OTHER INFORMATION: /mod_base=i ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( x i ) SEQUENCE DESCRIPTION: SEQ ID NO:1:

```
AARACNTAYG AYCTNGARGT NTGGATHCC                                    29
```

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( x i ) SEQUENCE DESCRIPTION: SEQ ID NO:2:

```
CCRTCNGCYT GYTGRTARTT YTC                                          23
```

( 2 ) INFORMATION FOR SEQ ID NO:3:

( i ) SEQUENCE CHARACTERISTICS:
        ( A ) LENGTH: 1260 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1257

( x i ) SEQUENCE DESCRIPTION: SEQ ID NO:3:

```
GTG ATC GAC CTG AAG CTG CTT CGT GAA AAC CCC GAC GCG GTA CGC CGC    48
Met Ile Asp Leu Lys Leu Leu Arg Glu Asn Pro Asp Ala Val Arg Arg
 1               5                  10                  15

TCA CAA CTC AGC CGC GGC GAG GAC CCG GCG CTG GTA GAT GCC CTG CTG    96
Ser Gln Leu Ser Arg Gly Glu Asp Pro Ala Leu Val Asp Ala Leu Leu
            20                  25                  30
```

```
ACG  GCC  GAC  GCC  GCC  CGC  CGG  GCC  GTG  ATC  TCG  ACC  GCC  GAT  TCG  TTA       144
Thr  Ala  Asp  Ala  Ala  Arg  Arg  Ala  Val  Ile  Ser  Thr  Ala  Asp  Ser  Leu
          35                  40                       45

CGG  GCC  GAG  CAG  AAA  GCC  GCC  AGC  AAA  AGC  GTG  GGT  GGC  GCG  TCT  CCC       192
Arg  Ala  Glu  Gln  Lys  Ala  Ala  Ser  Lys  Ser  Val  Gly  Gly  Ala  Ser  Pro
          50                  55                       60

GAA  GAG  CGC  CCG  CCG  CTG  CTG  CGG  CGC  GCG  AAG  GAA  CTC  GCC  GAG  CAG       240
Glu  Glu  Arg  Pro  Pro  Leu  Leu  Arg  Arg  Ala  Lys  Glu  Leu  Ala  Glu  Gln
65                            70                  75                            80

GTC  AAA  GCC  GCT  GAG  GCC  GAC  GAG  GTC  GAA  GCG  GAG  GCG  GCG  TTC  ACC       288
Val  Lys  Ala  Ala  Glu  Ala  Asp  Glu  Val  Glu  Ala  Glu  Ala  Ala  Phe  Thr
                    85                  90                       95

GCG  GCG  CAC  CTG  GCG  ATC  TCG  AAT  GTC  ATC  GTG  GAC  GGG  GTA  CCC  GCC       336
Ala  Ala  His  Leu  Ala  Ile  Ser  Asn  Val  Ile  Val  Asp  Gly  Val  Pro  Ala
               100                      105                      110

GGC  GGG  GAG  GAC  GAC  TAC  GCG  GTG  CTC  GAC  GTC  GTC  GGC  GAG  CCC  AGC       384
Gly  Gly  Glu  Asp  Asp  Tyr  Ala  Val  Leu  Asp  Val  Val  Gly  Glu  Pro  Ser
               115                      120                      125

TAC  CTC  GAG  AAC  CCC  AAG  GAC  CAC  CTG  GAG  CTC  GGC  GAG  TCG  CTG  GGC       432
Tyr  Leu  Glu  Asn  Pro  Lys  Asp  His  Leu  Glu  Leu  Gly  Glu  Ser  Leu  Gly
          130                      135                      140

CTG  ATC  GAC  ATG  CAG  CGC  GGC  GCC  AAG  GTG  TCG  GGT  TCA  CGG  TTC  TAC       480
Leu  Ile  Asp  Met  Gln  Arg  Gly  Ala  Lys  Val  Ser  Gly  Ser  Arg  Phe  Tyr
145                      150                      155                           160

TTC  CTG  ACC  GGT  CGG  GGT  GCC  CTA  CTG  CAG  CTT  GGA  TTG  CTG  CAG  CTG       528
Phe  Leu  Thr  Gly  Arg  Gly  Ala  Leu  Leu  Gln  Leu  Gly  Leu  Leu  Gln  Leu
                    165                      170                      175

GCG  CTG  AAG  CTA  GCC  GTC  GAC  AAC  GGC  TTT  GTC  CCT  ACG  ATC  CCG  CCG       576
Ala  Leu  Lys  Leu  Ala  Val  Asp  Asn  Gly  Phe  Val  Pro  Thr  Ile  Pro  Pro
               180                      185                      190

GTG  CTG  GTG  CGC  CCG  GAA  GTG  ATG  GTA  GGC  ACG  GGA  TTT  CTA  GGC  GCC       624
Val  Leu  Val  Arg  Pro  Glu  Val  Met  Val  Gly  Thr  Gly  Phe  Leu  Gly  Ala
          195                      200                      205

CAC  GCC  GAG  GAG  GTG  TAC  CGG  GTA  GAG  GGC  GAC  GGC  CTC  TAC  CTT  GTG       672
His  Ala  Glu  Glu  Val  Tyr  Arg  Val  Glu  Gly  Asp  Gly  Leu  Tyr  Leu  Val
210                      215                      220

GGC  ACC  TCC  GAG  GTA  CCG  CTG  GCG  GGG  TAT  CAC  TCC  GGC  GAG  ATT  CTG       720
Gly  Thr  Ser  Glu  Val  Pro  Leu  Ala  Gly  Tyr  His  Ser  Gly  Glu  Ile  Leu
225                      230                      235                           240

GAC  CTT  TCC  CGC  GGG  CCG  CTG  CGG  TAT  GCG  GGC  TGG  TCG  TCG  TGT  TTC       768
Asp  Leu  Ser  Arg  Gly  Pro  Leu  Arg  Tyr  Ala  Gly  Trp  Ser  Ser  Cys  Phe
                    245                      250                      255

CGA  CGT  GAG  GCC  GGC  AGC  CAT  GGC  AAG  GAC  ACG  CGC  GGC  ATC  ATC  CGG       816
Arg  Arg  Glu  Ala  Gly  Ser  His  Gly  Lys  Asp  Thr  Arg  Gly  Ile  Ile  Arg
               260                      265                      270

GTG  CAC  CAG  TTC  GAC  AAA  GTC  GAG  GGC  TTC  GTC  TAC  TGC  ACA  CCG  GCC       864
Val  His  Gln  Phe  Asp  Lys  Val  Glu  Gly  Phe  Val  Tyr  Cys  Thr  Pro  Ala
          275                      280                      285

GAC  GCG  GAG  CAC  GAA  CAT  GAG  CGG  CTG  CTG  GGC  TGG  CAG  CGC  CAG  ATG       912
Asp  Ala  Glu  His  Glu  His  Glu  Arg  Leu  Leu  Gly  Trp  Gln  Arg  Gln  Met
          290                      295                      300

CTG  GCA  CGC  ATC  GAG  GTG  CCG  TAT  CGG  GTC  ATC  GAC  GTG  GCC  GCG  GGT       960
Leu  Ala  Arg  Ile  Glu  Val  Pro  Tyr  Arg  Val  Ile  Asp  Val  Ala  Ala  Gly
305                      310                      315                           320

GAT  CTC  GGC  TCG  TCG  GCC  GCC  CGC  AAG  TTC  GAC  TGC  GAG  GCG  TGG  ATT      1008
Asp  Leu  Gly  Ser  Ser  Ala  Ala  Arg  Lys  Phe  Asp  Cys  Glu  Ala  Trp  Ile
                    325                      330                      335

CCG  ACG  CAG  GGG  GCC  TAT  CGC  GAG  CTG  ACG  TCG  ACG  TCG  AAC  TGC  ACC      1056
Pro  Thr  Gln  Gly  Ala  Tyr  Arg  Glu  Leu  Thr  Ser  Thr  Ser  Asn  Cys  Thr
               340                      345                      350
```

| | | | | | | | | | | | | | | | | |
|---|---|---|---|---|---|---|---|---|---|---|---|---|---|---|---|---|
| ACC | TTT | CAG | GCG | CGC | CGG | TTG | GCG | ACC | CGC | TAC | CGG | GAT | GCC | AGC | GGC | 1104 |
| Thr | Phe | Gln | Ala | Arg | Arg | Leu | Ala | Thr | Arg | Tyr | Arg | Asp | Ala | Ser | Gly | |
| | | 355 | | | | | 360 | | | | | 365 | | | | |
| AAG | CCG | CAG | ATC | GCG | GCC | ACC | CTC | AAC | GGA | ACG | CTG | GCC | ACC | ACC | CGG | 1152 |
| Lys | Pro | Gln | Ile | Ala | Ala | Thr | Leu | Asn | Gly | Thr | Leu | Ala | Thr | Thr | Arg | |
| | 370 | | | | | 375 | | | | | 380 | | | | | |
| TGG | CTG | GTT | GCG | ATC | CTG | GAG | AAC | CAC | CAG | CGG | CCC | GAC | GGC | AGC | GTT | 1200 |
| Trp | Leu | Val | Ala | Ile | Leu | Glu | Asn | His | Gln | Arg | Pro | Asp | Gly | Ser | Val | |
| 385 | | | | | 390 | | | | | 395 | | | | | 400 | |
| AGA | GTC | CCG | GAC | GCA | CTG | GTT | CCG | TTC | GTG | GGT | GTC | GAA | GTG | CTG | GAG | 1248 |
| Arg | Val | Pro | Asp | Ala | Leu | Val | Pro | Phe | Val | Gly | Val | Glu | Val | Leu | Glu | |
| | | | | 405 | | | | | 410 | | | | | 415 | | |
| CCG | GTC | GCT | TAG | | | | | | | | | | | | | 1260 |
| Pro | Val | Ala | | | | | | | | | | | | | | |

(2) INFORMATION FOR SEQ ID NO:4:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Ile | Asp | Leu | Lys | Leu | Leu | Arg | Glu | Asn | Pro | Asp | Ala | Val | Arg | Arg |
| 1 | | | | 5 | | | | | 10 | | | | | 15 | |
| Ser | Gln | Leu | Ser | Arg | Gly | Glu | Asp | Pro | Ala | Leu | Val | Asp | Ala | Leu | Leu |
| | | | 20 | | | | | 25 | | | | | 30 | | |
| Thr | Ala | Asp | Ala | Ala | Arg | Arg | Ala | Val | Ile | Ser | Thr | Ala | Asp | Ser | Leu |
| | | 35 | | | | | 40 | | | | | 45 | | | |
| Arg | Ala | Glu | Gln | Lys | Ala | Ala | Ser | Lys | Ser | Val | Gly | Gly | Ala | Ser | Pro |
| | 50 | | | | | 55 | | | | | 60 | | | | |
| Glu | Glu | Arg | Pro | Pro | Leu | Leu | Arg | Arg | Ala | Lys | Glu | Leu | Ala | Glu | Gln |
| 65 | | | | | 70 | | | | | 75 | | | | | 80 |
| Val | Lys | Ala | Ala | Glu | Ala | Asp | Glu | Val | Glu | Ala | Glu | Ala | Ala | Phe | Thr |
| | | | | 85 | | | | | 90 | | | | | 95 | |
| Ala | Ala | His | Leu | Ala | Ile | Ser | Asn | Val | Ile | Val | Asp | Gly | Val | Pro | Ala |
| | | | 100 | | | | | 105 | | | | | 110 | | |
| Gly | Gly | Glu | Asp | Asp | Tyr | Ala | Val | Leu | Asp | Val | Val | Gly | Glu | Pro | Ser |
| | | 115 | | | | | 120 | | | | | 125 | | | |
| Tyr | Leu | Glu | Asn | Pro | Lys | Asp | His | Leu | Glu | Leu | Gly | Glu | Ser | Leu | Gly |
| | 130 | | | | | 135 | | | | | 140 | | | | |
| Leu | Ile | Asp | Met | Gln | Arg | Gly | Ala | Lys | Val | Ser | Gly | Ser | Arg | Phe | Tyr |
| 145 | | | | | 150 | | | | | 155 | | | | | 160 |
| Phe | Leu | Thr | Gly | Arg | Gly | Ala | Leu | Leu | Gln | Leu | Gly | Leu | Leu | Gln | Leu |
| | | | | 165 | | | | | 170 | | | | | 175 | |
| Ala | Leu | Lys | Leu | Ala | Val | Asp | Asn | Gly | Phe | Val | Pro | Thr | Ile | Pro | Pro |
| | | | 180 | | | | | 185 | | | | | 190 | | |
| Val | Leu | Val | Arg | Pro | Glu | Val | Met | Val | Gly | Thr | Gly | Phe | Leu | Gly | Ala |
| | | 195 | | | | | 200 | | | | | 205 | | | |
| His | Ala | Glu | Glu | Val | Tyr | Arg | Val | Glu | Gly | Asp | Gly | Leu | Tyr | Leu | Val |
| | 210 | | | | | 215 | | | | | 220 | | | | |
| Gly | Thr | Ser | Glu | Val | Pro | Leu | Ala | Gly | Tyr | His | Ser | Gly | Glu | Ile | Leu |
| 225 | | | | | 230 | | | | | 235 | | | | | 240 |
| Asp | Leu | Ser | Arg | Gly | Pro | Leu | Arg | Tyr | Ala | Gly | Trp | Ser | Ser | Cys | Phe |
| | | | | 245 | | | | | 250 | | | | | 255 | |
| Arg | Arg | Glu | Ala | Gly | Ser | His | Gly | Lys | Asp | Thr | Arg | Gly | Ile | Ile | Arg |

|   | 260 |   |   |   |   | 265 |   |   |   |   | 270 |   |   |
|---|---|---|---|---|---|---|---|---|---|---|---|---|---|
| Val | His | Gln | Phe | Asp | Lys | Val | Glu | Gly | Phe | Val | Tyr | Cys | Thr | Pro | Ala |
|   |   | 275 |   |   |   |   | 280 |   |   |   | 285 |   |   |
| Asp | Ala | Glu | His | Glu | His | Glu | Arg | Leu | Leu | Gly | Trp | Gln | Arg | Gln | Met |
|   |   | 290 |   |   |   |   | 295 |   |   |   | 300 |   |   |
| Leu | Ala | Arg | Ile | Glu | Val | Pro | Tyr | Arg | Val | Ile | Asp | Val | Ala | Ala | Gly |
| 305 |   |   |   |   | 310 |   |   |   |   | 315 |   |   |   | 320 |
| Asp | Leu | Gly | Ser | Ser | Ala | Ala | Arg | Lys | Phe | Asp | Cys | Glu | Ala | Trp | Ile |
|   |   |   |   | 325 |   |   |   |   | 330 |   |   |   |   | 335 |
| Pro | Thr | Gln | Gly | Ala | Tyr | Arg | Glu | Leu | Thr | Ser | Thr | Ser | Asn | Cys | Thr |
|   |   |   | 340 |   |   |   |   | 345 |   |   |   | 350 |   |   |
| Thr | Phe | Gln | Ala | Arg | Arg | Leu | Ala | Thr | Arg | Tyr | Arg | Asp | Ala | Ser | Gly |
|   |   | 355 |   |   |   |   | 360 |   |   |   |   | 365 |   |   |
| Lys | Pro | Gln | Ile | Ala | Ala | Thr | Leu | Asn | Gly | Thr | Leu | Ala | Thr | Thr | Arg |
|   | 370 |   |   |   |   | 375 |   |   |   | 380 |   |   |   |   |
| Trp | Leu | Val | Ala | Ile | Leu | Glu | Asn | His | Gln | Arg | Pro | Asp | Gly | Ser | Val |
| 385 |   |   |   |   | 390 |   |   |   | 395 |   |   |   |   | 400 |
| Arg | Val | Pro | Asp | Ala | Leu | Val | Pro | Phe | Val | Gly | Val | Glu | Val | Leu | Glu |
|   |   |   |   | 405 |   |   |   |   | 410 |   |   |   |   | 415 |
| Pro | Val | Ala |

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( x i ) SEQUENCE DESCRIPTION: SEQ ID NO:5:

CGCGGATCCA TGATCGACCT GAAGCTG     27

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( x i ) SEQUENCE DESCRIPTION: SEQ ID NO:6:

AAGGAATTCC GCGCTCGCGA TCGCC     25

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( x i ) SEQUENCE DESCRIPTION: SEQ ID NO:7:

GGGAAATCCA TATGATCGAC CTGAAGCTG     29

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( x i ) SEQUENCE DESCRIPTION: SEQ ID NO:8:

CTTCGGATCC CGCTAAGCGA CCGGCTC          27

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: modified_base
        ( B ) LOCATION: 18
        ( D ) OTHER INFORMATION: /mod_base=i ( x i ) SEQUENCE DESCRIPTION: SEQ ID NO:9:

GARAA YTAYC ARCARGCN-
GA YGG          23

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR Primer"

( i x ) FEATURE:
        ( A ) NAME/KEY: modified_base
        ( B ) LOCATION: 6
        ( D ) OTHER INFORMATION: /mod_base=i ( x i ) SEQUENCE DESCRIPTION: SEQ ID NO:10:

CCRTCNGC YT G YTGRTART-
T YTC          23

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

Lys Thr Tyr Asp Leu Glu Val Trp Ile Pro
1                5                        10

( 2 ) INFORMATION FOR SEQ ID NO:12:

( i ) SEQUENCE CHARACTERISTICS:
        ( A ) LENGTH: 10 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Lys Lys Tyr Asp Leu Glu Ala Trp Phe Pro
    1               5                   10

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Lys Lys Leu Asp Leu Glu Ala Trp Phe Pro
    1               5                   10

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Glu Asn Tyr Gln Gln Ala Asp Gly
    1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Glu Asn Tyr Gln Thr Glu Asp Gly
    1               5

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Glu Asn Tyr Gln Thr Glu Lys Gly
    1               5

RECOMBINANT MYCOBACTERIAL SERYL-TRNA SYNTHETASE GENES, TESTER STRAINS AND ASSAYS

BACKGROUND OF THE INVENTION

Mycobacteria are slow-growing aerobic bacteria characterized by their surface glycolipids, and by the high G-C content of their DNA (>63%). Organisms of the genus Mycobacterium include more than 30 well-characterized members and many that are as yet unclassified. Most are not pathogenic for humans, but among the mycobacteria are the etiologic agents for leprosy (*M. leprae*) and for tuberculosis (*M. tuberculosis*), the leading cause of death in the world from an infectious disease (Bloom, B. R. and Murray, C. J. L., *Science*, 257:1055–1064 (1992)).

It has been estimated that as much as one third of the population of the world is infected with *M. tuberculosis*, and that tuberculosis (TB) is responsible for one in four avoidable adult deaths in developing countries (Murray, C. J. L. et al., pp. 233–259 In *Disease Control Priorities in Developing Countries*, D. T. Jamison et al., Eds. (Oxford Univ. Press, New York, 1993). Since the 1980s the number of new cases of TB infections has steadily increased both in the US and in Europe. Individuals infected with the human immunodeficiency virus (HIV) are particularly susceptible to infection with *M. tuberculosis*, a growing problem that threatens the control of the spread of tuberculosis.

Infection caused by drug-sensitive strains of *M. tuberculosis* has been successfully treated by using a combination of isoniazid, rifampicin and pyrazinamide. However, in cities worldwide, the emergence of multidrug resistant isolates of *M. tuberculosis* is becoming alarming. The fatality rate for drug-resistant TB is 50%. According to the World Health Organization, almost 20% of the isolates tested in New York City in 1992 were resistant to both isoniazid and rifampicin.

It would be a great advantage in the control of diseases caused by the Mycobacteria to expand the number of target molecules whose function could be inhibited by antibiotic agents.

SUMMARY OF THE INVENTION

The invention relates to isolated and/or recombinant nucleic acids which encode seryl-tRNA (Ser tRNA) synthetases (SerRSs) of mycobacterial origin. The invention also relates to recombinant DNA constructs and vectors containing DNA having a sequence which encodes a seryl-tRNA synthetase of mycobacterial origin, or portions of the enzyme. These nucleic acids and DNA constructs can be used to produce recombinant seryl-tRNA synthetase of mycobacterial origin.

A further embodiment of the invention is antisense nucleic acid which can hybridize to the nucleic acid which encodes the seryl-tRNA synthetase of mycobacteria. In cells, antisense nucleic acid can inhibit the function of an RNA which encodes the seryl-tRNA synthetase of mycobacteria.

The invention also relates to proteins or polypeptides, referred to herein as isolated, recombinant mycobacterial seryl-tRNA synthetases. These enzymes are useful in biochemical separation of serine and quantitations of serine and ATP. Antibodies which bind to these enzymes can be made and can be used in the purification and study of the enzyme.

The recombinant mycobacterial seryl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by the introduced cloned gene. In this way, potential inhibitors can be screened for antimicrobial or antibiotic effects, without having to employ slow-growing, pathogenic strains of mycobacteria.

DETAILED DESCRIPTION OF THE INVENTION

The aminoacyl-tRNA synthetases are enzymes with the common general function of catalyzing the following reaction:

(aaRS=aminoacyl-tRNA synthetase; aa=amino acid; ATP= adenosine 5'-triphosphate; AMP=adenosine 5'-monophosphate; $PP_i$=inorganic pyrophosphate) The second (aminoacylation) step is often referred to as "charging" the tRNA.

Generally, in each bacterial organism, there are 20 different aaRSs, one specific for each amino acid. For each amino acid, eucaryotic organisms also have 20 different cytoplasmic aaRSs, and generally also encode a separate set of mitochondrial aaRSs. Each aminoacyl-tRNA synthetase enzyme recognizes and reacts with a specific amino acid and one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS.

Although the isolation of a complete aminoacyl-tRNA synthetase gene from an organism of the genus Mycobacterium has not been reported previously, tRNA synthetases of *E. coli* have been studied. Based on conserved sequences and structural motifs, the 20 tRNA synthetases are divided into two classes of 10 enzymes each (see, e.g., Burbaum, J. J. and Schimmel, P., *J. Biol. Chem.*, 266(26):16965–16968 (1991); Shepard, A., et al., *Proc. Natl. Acad. Sci. U.S.A.* 89:9964–9968 (1992); Hou, Y. -M., et al., *Proc. Natl. Acad. Sci. U.S.A.* 88:976–980 (1991); Shiba, K., et al., *Proc. Natl. Acad. Sci. USA* 89:1880–1884 (1992); Starzyk, R. M., et al., *Science* 237:1614–1618 (1987); Schimmel, P., et al., *Protein Science* 1:1387–1391 (1992); Eriani, G., et al., *Nucleic Acids Res.* 19:265–269 (1991); see also Cusack, S. C. et al., *Nature* 347:249–255 (1990); Cusack S. M. et al., *Nucleic Acids Res.* 19:3489–3498 (1991); Biou, V. et al., *Science* 263:1404–1410 (1994); Belrhali, H. et al., *Science* 263: 1432–1436 (1994), regarding Class II seryl-tRNA synthetases).

Aminoacyl-tRNA synthetases are believed to be among the earliest proteins to have arisen in evolution. For this reason, and because the fidelity of these enzymes for their substrates must be high to accurately carry out the genetic code in protein biosynthesis, biologists have long studied the structures of these enzymes and their interactions with their substrates. Because the amino acid sequences of the tRNA synthetases have diverged over evolutionary time, significant differences exist between the structures of the enzymes from mammals (e.g., human, bovine) and mammalian pathogens. These differences can be exploited by finding inhibitors of aaRS activity which specifically target a tRNA synthetase of a pathogenic organism, and which may further have specific antimicrobial activity.

Examples of such inhibitors are already known. Pseudomonic acid and furanomycin have been found to inhibit bacterial isoleucyl-tRNA synthetases (Hughes, J. and Mellows, G., *Biochem J.*, 176:305–318 (1978)). Pseudomonic acid, an antibiotic which is in use as a human therapeutic agent, significantly inhibits binding of isoleucine to *E. coli* isoleucyl-tRNA synthetase and competitively inhibits aminoacylation by the enzyme, while it only weakly inhibits the aminoacylation of yeast tRNA$^{Ile}$ by rat liver IleRS (Hughes, J. and Mellows, G., *Biochem. J.* 191:209–219 (1980)).

Isolation of a Gene Encoding Ser tRNA Synthetase from *M. tuberculosis*

One combination of degenerate primers (Kiyo-142 (SEQ ID NO:1) and Kiyo-145 N) (SEQ ID NO:2) was successfully used to amplify a 212 basepair fragment from *M. tuberculosis* (Erdman H37Rv) genomic DNA by PCR (polymerase chain reaction) methodologies (Table 1; Example 1). Using standard Southern hybridization techniques under stringent temperature conditions, the radiolabeled PCR fragment hybridized to EcoRI digested *M. tuberculosis* (Erdman H37Rv and H37Ra) genomic DNA, but did not hybridize to digested *E. coli* genomic DNA. The PCR fragment was sequenced, revealing a high G-C content (about 65%) which is typical of mycobacterial genomes. Using random protein data base searches, the translated protein was found to be homologous to portions of Ser tRNA synthetases from *T. thermophilus, E. coli, S. cerevisae*, and *Cricetelus griseus*, with homologies over those regions ranging from 30 to 40%.

A λgt11 *M. tuberculosis* library was screened by hybridization with a [$^{32}$P]-labeled *M. tuberculosis* PCR fragment (Example 2). Approximately 100,000 plaques were analyzed, yielding six positive plaques. The positive plaques were purified and the DNA isolated. One of the plaques was digested with EcoRI, yielding a 3.7 kb *M. tuberculosis* insert, which was cloned into a pBSKS+ vector (Stratagene) for characterization. Internal sequencing primers were designed based on the *M. tuberculosis* Ser tRNA synthetase PCR fragment. The λgt11 insert contained the entire gene, which was sequenced in a sequential manner.

Characterization of *M. tuberculosis* Ser tRNA Synthetase

The gene encoding *M. tuberculosis* Ser tRNA synthetase and its flanking sequences were sequenced (Example 3). FIGS. 1A–1B (SEQ ID NO:3) shows the sequence of an open-reading frame of 1,257 bases, beginning with a GTG start codon (position 1, SEQ ID NO:3). GTG (GUG in the mRNA) initiation codons have been observed in *M. tuberculosis* genes as well as in other organisms. However, where a codon other than AUG has been observed, invariably, the amino acid used for initiation has been determined to be methionine (Varshney, U. and U. L. RajBhandary, *Proc. Natl. Acad. Sci. USA*, 87:1586–1590 (1990)). Accordingly, FIG. 2 SEQ ID NO:4 shows a methionine at the N-terminus of the encoded protein. For expression in *E. coli*, the GTG at position 1 was altered to ATG. The gene was G-C rich (67%), which is typical of mycobacterial genes.

The translated protein was 419 amino acids (SEQ ID NO:4). Random protein data bases searches using the translated complete *M. tuberculosis* Ser tRNA synthetase sequence showed that the protein was most closely related to Ser tRNA synthetase from *T. thermophilus*, followed by *B. subtilus*. Less homology was found to the Ser tRNA synthetase of *S. cerevisiae* (cytoplasmic), *Coxiella burnetii*, and *E. coli*.

Ser tRNA synthetase is a class II aminoacyl tRNA synthetase. The class II tRNA synthetases have been defined by three short sequence motifs that are denoted motif 1, motif 2, and motif 3. These regions help construct parts of the active site as well as the oligomerization region which is crucial for serylation. *E. coli* and *T. thermophilus* Ser tRNA synthetases have been crystallized in the presence and absence of $tRNA^{Ser}$ and evaluated by X-ray diffraction (Cusack, S. et al., In: *The Translation Apparatus, Nierhaus, K., ed.*, (Springer: Berlin) 1993). The X-ray crystal structure shows that the N-terminus of the protein forms a long α-helical protrusion which is intimately involved in tRNA recognition. In particular, the structure of the $tRNA^{Ser}$ is unique in that it has a long variable loop which interacts specifically with the α-helical region of Ser tRNA synthetase and is essential for discrimination from other tRNAs. The central and C-terminal regions contain the three conserved motifs (motifs 1, 2, and 3) which are important in aminoacyl-adenylation and oligomerization. The *M. tuberculosis* motifs were found to share sequence similarity with the corresponding motifs of *Thermus thermophilus* and *Bacillus subtilis* Ser tRNA synthetases.

Expression of *M. tuberculosis* Ser tRNA Synthetase

*M. tuberculosis* Ser tRNA synthetase was expressed (Example 3) as judged by analysis of crude protein extracts on SDS-polyacrylamide gels using four strains carrying four different expression vectors. The pJZS301 plasmid was constructed using a pET-15b vector which expresses the Ser tRNA synthetase as a fusion protein with a histidine tail (see pET System Manual from Novagen, Madison, Wis. for procedures to make and purify histidine tail fusion proteins; for review see Arnold, F. H., et al., *Bio/Technology* 9:151–156 (1991)). The His-tail Ser tRNA synthetase was expressed under the control of the T7 promoter in one hour after induction with IPTG. The fusion protein was estimated to be about about 48 kD and was primarily sequestered in inclusion bodies. The protein was purified to homogeneity under denaturing conditions by affinity chromotagraphy using a nickel column (Example 4). The final product is stable and soluble. The His tail Ser tRNA synthetase was tested for serylation of *E. coli* $tRNA^{Ser}$ transcript (Example 5) and was found to be inactive under the conditions used.

*M. tuberculosis* Ser tRNA synthetase was also expressed as a GST (glutathione-S-transferase) fusion protein using the pJZS201 and pJZS220 plasmids which were constructed from pGEX-4T-2 and pGEX-KT respectively. Both GST-Ser tRNA synthetases were expressed under the pTac promoter as a 72 kD protein. The fusion protein encoded by pJZ201 was purifed to homogeneity over a glutathione agarose column by affinity chromatography as described in Example 4. The GST-Ser tRNA synthetase was tested for aminoacylation activity as described above, but found to be inactive under the conditions used.

There may be several reasons that no aminoacylation activity could be detected. Since the expressed protein is found in inclusion bodies, denaturing conditions are required for protein recovery. Re-solubilization of the Ser tRNA synthetase may result in improperly-folded protein. Also, the histidine tail and GST moiety are fused to the N-terminus of Ser tRNA synthetase in the fusion proteins. This region of the protein lies at an interface which is important for tRNA interactions. Thus, the fusion may interfere with tRNA binding and/or enzymatic activation.

Another possibility is that the enzyme contains a PCR-induced mutation which renders it inactive. The entire gene was cloned into the expression vectors using PCR to modify the ends of the gene to facilitate cloning and expression. However, the gene contains two convenient internal restriction sites, PpuMI and DraIII, which permit a 1.08 kb PCR-generated portion of the gene to be exchanged with the corresponding genomic DNA.

*M. tuberculosis* Ser tRNA synthetase has also been expressed from pJZS320, which is designed so that the Ser tRNA synthetase is not expressed as a fusion protein (see Example 3). Upon expression, this protein was found to be sequestered in inclusion bodies.

Example 6 describes a protocol which has been used successfully to recover active *M. tuberculosis* GST-leucyl-tRNA synthetase fusion protein from the soluble fraction. This protocol can be applied to the Ser tRNA synthetase fusion proteins described here or to Ser tRNA synthetase proteins, such as the protein encoded by pJZS320.

Nucleic Acids, Constructs and Vectors

The present invention relates to isolated and/or recombinant (including, e.g., essentially pure) nucleic acids having sequences which encode a mycobacterial seryl-tRNA synthetase, or a portion of a mycobacterial seryl-tRNA synthetase. In one embodiment, the nucleic acid or portion thereof encodes a protein or polypeptide having at least one function characteristic of a mycobacterial seryl-tRNA synthetase, such as a catalytic activity (e.g., catalysis of aminoacyl-adenylate formation, catalysis of aminoacylation of a tRNA with serine) and/or binding function (e.g., tRNA-, amino acid-, or ATP-binding). The present invention also relates more specifically to isolated and/or recombinant nucleic acids or a portion thereof having sequences which encode seryl-tRNA synthetase of *M. tuberculosis* or a portion thereof.

The invention further relates to isolated and/or recombinant nucleic acids that are characterized by (1) their ability to hybridize to a nucleic acid having the sequence in SEQ ID NO:3 (having a GTG initiation codon as shown or an ATG initiator codon) or its complement, or (2) by their ability to encode a polypeptide of the amino acid sequence in FIG. 2 or functional equivalents thereof (i.e., a polypeptide which aminoacylates the isoaccepting cognate serine tRNAs of *M. tuberculosis* with serine), or (3) by both characteristics. In one embodiment, the percent amino acid sequence similarity between the polypeptide of SEQ ID NO:4 and functional equivalents thereof is at least about 45% ($\geq$45%). In a preferred embodiment, functional equivalents of the polypeptide of SEQ ID NO:4 share at least about 50% sequence similarity with the polypeptide of SEQ ID NO:4. More preferably, the percent amino acid sequence similarity between the polypeptide of SEQ ID NO:4 and functional equivalents thereof is at least about 60%, and still more preferably, at least about 70%. Isolated and/or recombinant nucleic acids meeting these criteria comprise nucleic acids having sequences identical to sequences of naturally occurring mycobacterial SerRS and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for homology.

Isolated and/or recombinant nucleic acids that are characterized by their ability to hybridize to a nucleic acid having the sequence in SEQ ID NO:3 or its complement (e.g. under high or moderate stringency conditions) may further encode a protein or polypeptide having at least one function characteristic of a mycobacterial seryl-tRNA synthetase, such as a catalytic activity (e.g., aminoacyl-adenylate formation, aminoacylation of a tRNA with serine) and/or binding function (e.g., tRNA-, amino acid-, or ATP-binding). The catalytic or binding function of a protein or polypeptide encoded by hybridizing nucleic acid may be detected by standard enzymatic assays for activity or binding (e.g., assays which monitor aminoacyl-adenylate formation, aminoacylation of tRNA). Functions characteristic of seryl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide of the amino acid sequence in SEQ ID NO:4 or functional equivalents thereof.

Nucleic acids of the present invention can be used in the production of proteins or polypeptides. For example, DNA containing all or part of the coding sequence for mycobacterial seryl-tRNA synthetase, or DNA which hybridizes to the sequence in SEQ ID NO:3, and having either a GTG or an ATG initiation codon, or its complement, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a mycobacterial seryl- or aminoacyl-tRNA synthetase can also refer to one of two or more distinct subunits of said tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of the sequence in SEQ ID NO:3. For example, antisense nucleic acid can be complementary to a target nucleic acid having the sequence of in SEQ ID NO:3 or a portion thereof sufficient to allow hybridization. In another embodiment, the antisense nucleic acid is wholly or partially complementary to and can hybridize with a target nucleic acid which encodes a mycobacterial seryl-tRNA synthetase (e.g., *Mycobacterium tuberculosis* SerRS).

*M. tuberculosis* is the major causative agent of infectious tuberculosis in humans. Because advances in the understanding and treatment of this disease would be of tremendous benefit, it was the *mycobacterial species* selected for most of the experimental work described herein. However, the approaches described to isolate and manipulate the SerRS gene of *M. tuberculosis*, to construct vectors and host strains, and to produce and use the SerRS enzyme, can be applied to other members of the genus of Mycobacteria, including, but not limited to, pathogenic strains such as *M. leprae, M. kansasii, M. avium, M. intracellulare, M. bovis,* and *M. paratuberculosis,* or fast-growing, non-pathogenic strains, such as *M. smegmatis*. The entire *M. tuberculosis* seryl-tRNA synthetase gene described here, or sufficient portions thereof, including the fragments within the coding sequence which were produced by PCR, can be used as a probe in hybridization experiments to detect and recover homologous genes of the other mycobacterial species. This can be achieved using the procedures described herein or other suitable methods.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in mycobacterial cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein has at least one function characteristic of a mycobacterial seryl-tRNA synthetase, such as a catalytic activity (e.g., catalysis of aminoacyl-adenylate formation, catalysis of aminoacylation of a tRNA with serine) and/or binding function (e.g., tRNA-, amino acid-, or ATP-binding). As such, these proteins are referred to as seryl-tRNA synthetases of mycobacterial origin or mycobacterial seryl-tRNA synthetases, and include, for example, naturally occurring mycobacterial seryl-tRNA synthetases, variants of those proteins and/or portions thereof. Such variants include mutants differing by the addition, deletion or substitution of one or more amino acid residues, or modified polypeptides in which one or more residues is modified, and mutants comprising one or more modified residues.

In a particularly preferred embodiment, like naturally occurring mycobacterial seryl-tRNA synthetases, the mycobacterial seryl-tRNA synthetases of the present invention aminoacylate the isoaccepting cognate serine tRNAs of the mycobacterium with serine in a two-step reaction. For example, in the case of *M. tuberculosis*, an isolated mycobacterial seryl-tRNA synthetase is able to aminoacylate each of the isoaccepting species of cognate tRNA$^{Ser}$ of *M. tuberculosis* with serine. In the first step, mycobacterial seryl-tRNA synthetase catalyzes the covalent linkage of serine to ATP to form an adenylate complex (seryl-adenylate) with the release of pyrophosphate, and, in a second step, catalyzes the covalent linkage of serine to a specific tRNA recognized by the enzyme, releasing AMP.

The invention further relates to fusion proteins, comprising a mycobacterial seryl-tRNA synthetase (as described above) as a first moiety, linked to second moiety not occurring in the mycobacterial SerRS as found in nature. Thus, the second moiety can be an amino acid or polypeptide. The first moiety can be in an N-terminal location, C-terminal location or internal to the fusion protein. In one embodiment, the fusion protein comprises an *M. tuberculosis* seryl-tRNA synthetase as the first moiety, and a second moiety comprising a linker sequence and affinity ligand.

Fusion proteins can be produced by a variety of methods. For example, some embodiments can be produced by the insertion of a SerRS gene or portion thereof into a suitable expression vector, such as Bluescript SK +/− (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., Example 4; *Current Protocols in Molecular Biology* (Ausubel, F. M. et al., eds., Vol. 2, Suppl. 26, pp. 16.4.1–16.7.8 (1991)).

The invention also relates to isolated and/or recombinant portions of a seryl-tRNA synthetase of mycobacterial origin. A portion of a mycobacterial seryl-tRNA synthetase can also refer to one of two or more distinct subunits of said tRNA synthetase. Portions of the enzyme can be made which have full or partial function on their own, or which when mixed together (though fully, partially, or nonfunctional alone), spontaneously assemble with one or more other polypeptides to reconstitute a functional protein having at least one function characteristic of a mycobacterial seryl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coli* MetRS which can fold together to reconstitute an active enzyme capable of recognizing and charging tRNA in vitro and in vivo). Portions of the enzyme having at least one function characteristic of seryl-tRNA synthetase, such as a catalytic and/or binding function, can be made. Extensive studies on the structure and function of the aaRSs provide the basis for being able to divide the mycobacterial SerRS enzymes into functional domains (Schimmel, P., *Current Biology* 1:811–816 (1991)).

The sequences and structures of the catalytic domain of tRNA synthetases already purified and studied are the basis for dividing them into two distinct classes of ten enzymes each, Class I and Class II (Schimmel, P., *Ann. Rev. Biochem.* 56:125–158 (1987); Webster, T. A., et al., *Science* 226:1315–1317 (1984); Eriani, G. et al., *Nature* 347:203–206 (1990) and Cusack, S., et al., *Nature* 347:249–255 (1990)). Class I enzymes have a well-conserved N-terminal nucleotide binding fold responsible for amino acid binding, aminoacyl-adenylate formation, and tRNA acceptor helix docking. Within this domain are CP1 and CP2, segments of non-conserved amino acid sequence of lengths varying with the species of origin. Studies of the function of mutant aaRS gene products and analyses of the aligned amino acid sequences of aaRSs have revealed conserved and nonconserved regions and likely sites for interactions with other molecules (Shepard, A., et al., *Proc. Natl. Acad. Sci. USA* 89:9964–9968 (1992)). Extensive deletions could be made in the CP1-encoding region of the IleRS gene of *E. coli* without destroying activity of the mutant enzyme (Starzyk, R. M., et al., *Science* 237:1614–1618 (1987)), for example.

Joined to the class-defining domain is a second domain, idiosyncratic to the tRNA synthetase, which provides interactions with the parts of the tRNA which are distal to the amino acid attachment site. In some tRNA synthetases, this second domain interacts directly with the anticodon (Rould, M. A. et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in Class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Method of Producing Recombinant Mycobacterial SerRSs

Another aspect of the invention relates to a method to produce mycobacterial seryl-tRNA synthetase or a portion thereof and an expression system and host cells containing a vector appropriate for expression of the mycobacterial seryl-tRNA synthetase.

Cells that express a recombinant mycobacterial seryl-tRNA synthetase or a portion thereof can be made and grown in culture to produce the enzyme for isolation and purification. These cells can be procaryotic or eucaryotic. Examples of procaryotic cells that can be used to express mycobacterial seryl-tRNA synthetases include *Escherichia coli*, *Bacillus subtilis* and other bacteria. Examples of eucaryotic cells that can be used to express mycobacterial seryl-tRNA synthetases include yeasts, such as *Saccharomyces cerevisiae*, and other lower eucaryotic cells, and cells of higher eucaryotes such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a recombinant mycobacterial SerRS protein or portion thereof for isolation and purification, as a first step the gene encoding the SerRS can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for mycobacterial seryl-tRNA synthetase, and has the coding sequence under the control of transcription signals and linked to appropriate translation signals to permit translation of the SerRS, portion thereof, or of a fusion protein comprising SerRS or portion thereof. As a second step, the vector can then be introduced into cells by a method appropriate to the type of host cells (e.g., transformation, electroporation, infection). In a third step, for expression from the seryl-tRNA synthetase gene, the host cells can be maintained under appropriate conditions, e.g., in the presence of inducer, normal growth conditions, etc.).

As a particular example of the above approach to ultimately producing active mycobacterial seryl-tRNA synthetase, a gene encoding the mycobacterial SerRS can be integrated into the genome of a virus that enters the host cells. By infection of the host cells, the components of a system which permits the transcription and translation of the mycobacterial aaRS gene are present in the host cells. Alternatively, an RNA polymerase gene, inducer, or other component required to complete such a gene expression system may be introduced into the host cells already containing the mycobacterial SerRS gene, for example, by means of a virus that enters the host cells and contains the required component. The mycobacterial SerRS gene can be under the control of an inducible or constitutive promoter. The promoter can be one that is recognized by the non-mycobacterial host cell RNA polymerase. The promoter can, alternatively, be one that is recognized by a viral RNA polymerase and is transcribed following infection of the host cells with a virus.

Antibodies

The invention further relates to antibodies raised against an isolated and/or recombinant mycobacterial seryl-tRNA synthetase, including portions thereof (e.g., a peptide), which can specifically recognize and bind to the enzyme. These can be used in methods to purify the protein or portions thereof, or to selectively inactivate one of the enzyme's active sites, or to study other aspects of the enzyme's structure, for example. The term antibody is intended to encompass both polyclonal and monoclonal antibodies. The term antibody is also intended to encompass whole antibodies, biologically functional fragments thereof, and chimeric and humanized antibodies comprising portions from more than one species. Biologically functional antibody fragments which can be used are those fragments sufficient for binding of the antibody fragment to a mycobacterial SerRS to occur, such as Fab, Fv, Fab' and F(ab')$_2$ fragments. The chimeric antibodies can comprise proteins derived from two different species. The portions derived from two different species can be joined together chemically by conventional techniques or can be prepared as a single contiguous protein using genetic engineering techniques (See, e.g., Cabilly et al., U.S. Pat. No. 4,816,567, Neuberger, M. S. et al., WO 86/01533 and Winter, G. P., EP 0,239,400). DNA encoding the proteins of both portions of the chimeric antibody can be expressed to produce a contiguous protein.

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more mycobacterial seryl-tRNA synthetases.

Enzyme Assay

Upon the isolation of an aaRS gene from mycobacteria, the gene can then be put into an expression system for production, followed by isolation and testing of the enzyme in vitro. The isolated or purified mycobacterial aaRS can also be used in further structural studies that will allow for the design of antibiotics which specifically target the aaRS of mycobacteria, while not affecting or minimally affecting the mammalian (e.g., human) aaRSs. The design of these drugs will exploit the structural differences between the pathogen aaRS and the aaRSs of mammals, such as humans.

Furthermore, isolated, active mycobacterial aaRSs can be used in an in vitro method of screening for inhibitors of aminoacyl-tRNA synthetase activity in which the inhibitory effect of a compound is assessed by monitoring SerRS activity according to standard techniques. For example, inhibitors of isolated, active mycobacterial SerRS can be identified by the method. In one embodiment, the isolated enzyme is maintained under conditions suitable for seryl-adenylate formation, the enzyme is contaced with a compound to be tested, and formation of the aminoacyl-adenylate is monitored by standard assay. A reduction in the activity measured in the presence of compound, as compared with the activity in the absence of compound, is indicative of inhibition of SerRS activity by the compound. In another embodiment, formation of seryl-tRNA$^{Ser}$ is monitored in a standard aminoacylation assay. Inhibitors identified by enzymatic assay can be further assessed for antimicrobial activity using tester strains as described herein, or other suitable assays.

Binding Assay

Isolated, recombinant aaRS or a portion thereof, and suitable fusion proteins can be used in a method to select and identify compounds which bind specifically to mycobacterial aaRSs, such as M. tuberculosis Set tRNA synthetase, and which are potential inhibitors of aaRS activity. Compounds selected by the method can be further assessed for their inhibitory effect on aaRS activity and for antimicrobial activity.

In one embodiment, isolated or purified mycobacterial SerRS can be immobilized on a suitable affinity matrix by standard techniques, such as chemical cross-linking, or via an antibody raised against the isolated or purified mycobacterial SerRS and bound to a solid support. The matrix is packed in a column or other suitable container and is contacted with one or more compounds (e.g., a mixture) to be tested under conditions suitable for binding of compound to the SerRS. For example, a solution containing compounds is made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the aaRS, such as serine, ATP, tRNA$^{Ser}$ for SerRS, or other suitable molecules which competitively inhibit binding).

Fusion proteins comprising all of, or a portion of, a mycobacterial aaRS linked to a second moiety not occurring in the mycobacterial aaRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of a mycobacterial aaRS gene or portion thereof into a suitable expression vector, which encodes an affinity ligand (e.g., pGEX-4T-2 and pET-15b, encoding glutathione-S-transferase and His-Tag affinity ligands, respectively). The expression vector is introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein is immobilized on a suitable affinity matrix under conditions sufficient to bind the affinity ligand portion of the fusion protein to the matrix, and is contacted with one or more compounds (e.g., a mixture) to be tested, under conditions suitable for binding of compound to the aaRS portion of the bound fusion protein. Next, the affinity matrix with bound fusion protein is washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer is formulated to permit binding of the fusion protein to the affinity matrix, without significantly disrupting binding of specifically bound compounds. In this aspect, compound elution buffer is formulated to permit retention of the fusion protein by the affinity matrix, but is formulated to interfere with binding of the compound (s) tested to the aaRS portion of the fusion protein. For example, a change in the ionic strength or pH of the elution buffer can lead to release of compounds, or the elution buffer can comprise a release component or components designed to disrupt binding of compounds to the aaRS portion of the fusion protein (e.g., one or more substrates or substrate analogs which can disrupt binding of compounds to the aaRS portion of the fusion protein, such as serine, ATP, tRNA$^{Ser}$ for SerRS, or other suitable molecules which competitively inhibit binding).

Immobilization can be performed prior to, simultaneous with or after contacting the fusion protein with compound as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the aaRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the aaRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rebek et al., Process for Creating Molecular Diversity, U.S. Ser. No. 08/180,215, filed Jan. 12, 1994, relating to compounds without tags; see also, Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D. et al., *Nature* 346: 818–822 (1990); Bock, L. C. et al., *Nature* 355: 584–566 (1992); and Szostak, J. W., *Trends in Biochem. Sci.* 17:89–93 (March, 1992)) can also be screened according to the present method to select RNA or DNA molecules which bind to an aaRS, such as *M. tuberculosis* SerRS. Such molecules can be further assessed for antimicrobial effect upon introduction into a cell (e.g., by expression in the case of an RNA molecule selected by the method).

Tester strains

Nucleic acids of the present invention can also be used in constructing tester strains for in vivo assays of the effect on the activity of the mycobacterial enzyme of a substance which is added to tester strain cells. A tester strain comprises a host cell having a defect in a gene encoding a mycobacterial aaRS, and a heterologous mycobacterial aaRS gene which complements the defect in the host cell gene. Thus, complementation of a particular defective host cell aaRS gene by a heterologous mycobacterial aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

For example, temperature-sensitive alleles of the genes encoding cytoplasmic IleRS and MetRS have been described in *S. cerevisiae* (Hartwell, L. H., and McLaughlin, C. S., *J. Bacteriol.* 96:1664–1671 (1968)), and are available from the Yeast Genetic Stock Center (University of California-Berkeley; catalog nos. 342 and 19:3:4, respectively). Temperature sensitive serS (encoding SerRS) strains of *E. coli* have also been described (Low, B., et al., *J. Bacteriol.* 108:742–750 (1971); Clarke, S. J. et al., *J. Bacteriol.* 113:1096–1103 (1973); Härtlein, M. et al., *Nucl. Acids Res.*, 15(3):1005–1017 (1987)).

If the heterologous gene complements the inactivated host cell gene, such a cell can be used in a test of whether a substance that enters the cells specifically interacts with the mycobacterial tRNA synthetase (or a component in the pathway of tRNA synthetase gene expression) introduced for testing, to cause loss of function of the tested mycobacterial tRNA synthetase in those host cells. Thus, such cells are "tester strains." Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)). Cross-species complementation within the genus Mycobacterium can also serve as the basis for testing, for example, the aaRS enzymes of *M. tuberculosis* in *M. smegmatis*.

In tester cells to be used in an assay for chemical substances that can inhibit the function of a specific mycobacterial aaRS, the gene for the mycobacterial tRNA synthetase can, for example, physically replace the host aaRS gene or can be present in addition to a host aaRS gene that does not produce a functional product, and the mycobacterial gene whose gene product is to be tested complements the host gene. A substance to be tested is administered to the tester cells, and the viability or growth of such cells can be compared with that of cells of a suitable control.

Suitable host cells can be mycobacterial or non-mycobacterial host cells. As a tester strain comprises a host cell comprising a heterologous mycobacterial aaRS gene (i.e., one from a heterologous species), a suitable mycobacterial host cell is heterologous with respect to the species from which the mycobacterial gene to be tested is isolated. One feature of using a heterologous mycobacterial species as a host cell in a tester strain is that mycobacterial species are likely to be more similar to each other than to non-mycobacterial species with respect to their enzymatic and structural composition. *M. smegmatis* or other fast growing, non-pathogenic species of mycobacteria, are preferred mycobacterial species to use as hosts for the construction of tester strains such as those comprising a *M. tuberculosis* SerRS gene.

Preferred non-mycobacterial species to use as hosts for the construction of tester strains are *E. coli*, *S. cerevisiae*, and *B. subtilis*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene which is to be inactivated later, along with some selectable marker gene, can be constructed and introduced into cells. Then, an inactivating mutation can be caused in the chromosomal copy of the aaRS gene. One way to do this is by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel., P., *J. Biol. Chem.* 261(15):6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS. A test plasmid which is compatible with the maintenance plasmid, and which contains a mycobacterial aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against S. cerevisiae cells which have a first plasmid containing the URA3 gene), cells which survive by virtue of having a complementing mycobacterial aaRS gene on the second plasmid can be selected (Sikorsky, R. S. and Boeke, J. D., Methods in Enzymology 194:302–318 (1991)).

A number of E. coli strains already exist in which an aaRS gene has been inactivated by some method, in whole or in part, yielding an observable phenotypic defect which can be detectably complemented. For example, a null strain in which the gene encoding MetRS has been inactivated, and a mutant strain of E. coli in which the gene encoding MetRS has been conditionally inactivated, have been described (see Kim, et al., Proc. Natl. Acad. Sci. USA 90:10046–10050 (1993), describing a metG null strain of E. coli carrying a maintenance plasmid, MN9261/pRMS615); and Barker, D. G. et al. Eur. J. Biochem. 127:449–457 (1982) and Starzyk, R. M. et al., Biochemistry, 28:8479–8484 (1989), regarding a mutant strain having a methionine auxotrophy because the $K_m$ for methionine of the enzyme encoded by the chromosomal MetG allele is elevated). E. coli strains having a defect, such as a null mutation, in the seryl-tRNA synthetase gene can be constructed in a similar manner using the E. coli seryl-tRNA synthetase gene, which been cloned and sequenced (Härtlein, M. et al., Nucl. Acids Res., 15(3):1005–1017 (1987)).

Several S. cerevisiae strains have been constructed in which a gene encoding a mitochondrial aaRS has been inactivated (see, e.g., Edwards et al., Cell 51:643–649 (1987)), or a cytoplasmic aaRS has been cloned on a vector (see, e.g., Ludmerer et al., J. Biol. Chem. 262:10801–10806 (1987)). The gene encoding the cytoplasmic seryl-tRNA synthetase from S. cerevisiae (serS) has been cloned and sequenced (Weygand-Durasevic, I. et al., Nucl. Acids Res., 15(5): 1887–1904 (1987)).

The pathogenicity and long generation time of Mycobacterium tuberculosis (24 h) are major obstacles in the genetic manipulation of this organism. Thus, in another embodiment, a fast growing species of mycobacteria, such as Mycobacterium smegmatis (2–3 h), can be used as a host to construct a tester strain.

For example, an M. smegmatis host cell having a defect in the endogenous SerRS gene can be constructed. The seryl-tRNA synthetase gene from M. smegmatis can be obtained and analyzed (e.g., by restriction mapping, sequence analysis) in order to identify a suitable site or sites for the insertion of a spectinomycin resistance cassette or other suitable marker gene to disrupt expression of the gene. The cassette can inserted into the M. smegmatis SerRS gene to disrupt the gene at a single site (e.g., by ligation into a particular restriction site) or can replace all or part of the gene (e.g., by ligation into two restriction sites, with deletion of intervening M. smegmatis SerRS gene sequences). The resulting construct can be introduced into the M. smegmatis host by suitable methods, and homologous recombination between flanking sequences in the construct and on the chromosome leads to inactivation of the M. smegmatis gene. Introduction of a heterologous mycobacterial aaRS gene which can complement the host cell defect prior to or simultaneous with inactivation can yield a tester strain.

For example, a linear fragment comprising the M. smegmatis gene disrupted by the insertion of a spectinomycin resistance cassette can be used to electroporate M. smegmatis. Homologous recombination between this construct and the wild type gene on the chromosome can occur (Husson, R. N., et al., J. Bacteriol. 172:519–524 (1990)), inactivating the host gene. Simultaneous with the introduction of the linear fragment, M. smegmatis can be transformed with a suitable rescue plasmid, such as pAL5000 (Labidi, A., et al., Curr. Microbiol. 11:235–240 (1984)) into which a heterologous mycobacterial (e.g., M. tuberculosis) seryl-tRNA synthetase gene has been cloned, which replicates in mycobacteria. Selection of transformants can be performed on 7H media (formulated for the growth of M. smegmatis; see Husson, R. N., et al., J. Bacteriol. 172:519–524 (1990)) containing spectinomycin.

In another approach, a linear fragment containing the M. smegmatis gene disrupted by the insertion of a spectinomycin resistance cassette can be cloned into a pUC vector or other suitable vector which does not replicate in mycobacteria (see, e.g., Yanisch-Perron, C., et al., Gene 33:103–119 (1985) regarding pUC vectors). The resulting nonreplicable vector can be used to electroporate M. smegmatis simultaneously with a suitable rescue plasmid, such as pAL5000 into which a heterologous mycobacterial (e.g., M. tuberculosis) seryl-tRNA synthetase gene has been cloned. The nonreplicable vector will be lost; however, cells in which recombination between the wild type gene on the chromosome and the disrupted gene present on the nonreplicable vector has occurred prior to loss of the construct, leading to inactivation of the host cell SerRS gene, can be selected as indicated above.

Causing or selecting for a double crossover event which creates a deletion and insertion can be used in itself as a one-step method of constructing a tester strain in which a native aaRS gene is replaced by the corresponding mycobacterial gene whose gene product is to be tested. Endogenous recombination mechanisms have been used to advantage previously in E. coli, B. subtilis, M. smegmatis, and S. cerevisiae, among other organisms. This method depends on the ability of the mycobacterial gene to be tested to complement the native corresponding aaRS gene. This can be done by introducing into the cells double-stranded DNA having regions of homology to the DNA flanking the target native aaRS gene, and having between these regions a gene encoding a selectable marker as well as the mycobacterial aaRS gene intended to replace the native aaRS gene. The survival of cells expressing the selectable marker is indicative of expression of the introduced mycobacterial aaRS gene and complementation of the defect in the endogenous synthetase.

For example, a tester strain, useful for testing the effect of a compound on the function of SerRS expressed by an inserted M. tuberculosis gene, can be constructed in a one-step method. Optional positive and negative controls for this cross-species transformation can be used to show that the resulting strain depends on the SerRS gene from M. tuberculosis for growth and that this recombination event is not lethal. For example, B. subtilis cells made competent for transformation (Dubnau, D. and Davidoff-Abelson, R., J. Mol. Biol. 56:209–221 (1971)) can be transformed with a suitable construct, such as a linearized plasmid containing an insert. Generally, the construct includes a selectable marker gene for antibiotic resistance, or other suitable selectable marker. In one embodiment, a linearized plasmid which contains the M. tuberculosis SerRS gene and an antibiotic resistance gene, situated between sequences homologous to the flanking sequences of the endogenous serS gene of the host cells, is used to transform the host cell. For a positive control, the linearized plasmid can be constructed in a similar fashion, except that the native *B. subtilis* serS gene replaces the *M. tuberculosis* gene, such that a normal *B. subtilis* serS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous serS gene. Successful construction of a tester strain can also be confirmed by Southern analysis.

The yeast *S. cerevisiae* offers additional possibilities for genetic manipulations to create tester strains, relative to bacteria. For example, one-step gene disruptions can be performed in diploid cells using a DNA fragment comprising a copy of an aaRS containing a deletion of the aaRS gene and an insertion of a selectable marker in the deleted gene. For example, serS, the gene encoding cytoplasmic seryl-tRNA synthetase from *S. cerevisiae*, has been cloned and sequenced (Weygand-Durasevic, I. et al., *Nucleic Acids Res.* 15(5):1887–1904 (1987)). A suitable fragment can be introduced into a diploid cell to disrupt one chromosomal copy of the yeast gene. Successful integration of the deleted aaRS gene can be confirmed by Southern blotting and by tetrad analysis of the sporulated diploid cells. The diploid cells heterozygous for the chromosomal aaRS gene provide a diploid tester strain which can be transformed with a plasmid containing the mycobacterial aaRS gene. These cells can be sporulated and the haploid spores analyzed for rescue of the defective chromosomal aaRS by the mycobacterial aaRS gene.

In addition, those diploid cells that are found to contain one copy of the deleted chromosomal aaRS gene, as well as one functional copy, can be transformed with a maintenance plasmid which contains the corresponding wild type yeast aaRS gene and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid tester strain can then be transformed with a test plasmid which expresses a mycobacterial aaRS gene, and the maintenance plasmid can be selected against by growing this strain under appropriate conditions.

Examples of convenient yeast vectors for cloning include those in the pRS400 series (Christianson, T. W., et al. *Gene* 110:119–122 (1992)), pDAD1 and pDAD2, which contain a GAL1 promoter (Davis, L. I. and Fink, G. R., *Cell* 61:965–978 (1990)) and pEG (Mitchell, D. A., et al. *Yeast* 9:715–723 (1993)).

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains, having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho. As a result, these strains are unable to grow on non-fermentable carbon sources even if a complementing gene is introduced into the strain. Therefore, in a haploid strain having a defect in, for example, the yeast mitochondrial seryl-tRNA synthetase gene (e.g., a gene disruption with a cosegregating selectable marker constructed as indicated above), the haploid strain can be crossed with a rho$^+$ strain having a wild-type mitochondrial seryl-tRNA synthetase gene to restore the mitochondrial DNA. The resulting rho$^+$ diploid can then be transformed with a plasmid which encodes the wild-type yeast mitochondrial seryl-tRNA synthetase (i.e., a maintenance plasmid) and a second selectable marker. Following sporulation, progeny spores which carry the defective mitochondrial SerRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using the mycobacterial aminoacyl-tRNA synthetases.

For instance, a plasmid encoding a mycobacterial seryl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the mycobacterial gene can be monitored on a non-fermentable carbon source.

In another embodiment, a mitochondrial seryl-tRNA synthetase gene disruption with a cosegregating selectable marker can be constructed in diploid rho$^+$ strain (see e.g., Edwards, H. and P. Schimmel, *Cell*, 51:643–649 (1987)). A plasmid encoding a mycobacterial seryl-tRNA synthetase gene is introduced on a plasmid having a second selectable marker. Sporulation of a resulting diploid yields two progeny spores carrying the yeast mitochondrial seryl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the mycobacterial gene on the introduced plasmid is indicated by growth on non-fermentable carbon sources of spores carrying the disrupted seryl-tRNA synthetase gene.

In the case of a mitochondrial tester strain, the mycobacterial seryl-tRNA synthetase can be imported into mitochondria to achieve complementation of the mitochondrial defect. When it is necessary to achieve import or desirable to improve the efficiency of import of the mycobacterial seryl-tRNA synthetase in the non-mycobacterial host cell, a gene fusion can be constructed using a sequence encoding a mitochondrial targeting sequence which functions in the host cell. For example, a mitochondrial targeting sequence can be introduced at the amino-terminal end of the mycobacterial seryl-tRNA synthetase. In one embodiment in yeast, the mycobacterial SerRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., *J. Biol. Chem.*, 263:13097 (1988)). Expression of the construct yields a fusion protein with an N-terminally located cytochrome oxidase IV targeting signal joined to the mycobacterial SerRS protein.

If the construction methods described here are not successful initially, one or more natural or synthetic mycobacterial or other (e.g., procaryotic, such as a bacterial, or eukaryotic, such as a mammalian or fungal) tRNA gene(s) can be introduced into the host cell to provide one or more cognate tRNAs for the mycobacterial aaRS. The tRNA genes of many species have been cloned and sequenced (Steinberg, S., Misch, A. and M. Sprinzl, "Compilation of tRNA sequences and sequences of tRNA genes", *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous mycobacterial aminoacyl-tRNA synthetase gene present in the tester strain (i.e., the "test gene"), can serve as control strains. These control strains comprise a "control gene" which is an aminoacyl-tRNA synthetase gene other than the heterologous mycobacterial aaRS gene present in the tester strain (i.e., an aaRS gene from a different species, such as a heterologous mycobacterial species or non-mycobacterial (procaryotic or eukaryotic) species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having an *M. tuberculosis* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene", which, as indicated above, is an aaRS gene other than the test gene (i.e., an aaRS gene from a different species, such as a heterologous mycobacterial species or non-mycobacterial (procaryotic or eukaryotic) species). Furthermore, the control gene, which can be cytoplasmic or mitochondrial, encodes an aaRS specific for the same amino acid as the test gene (e.g., a seryl-tRNA synthetase control gene is used for a seryl-tRNA synthetase test gene).

Preferably, the control gene is selected from a species which is a host for the mycobacterial pathogen from which the test gene is derived, permitting the identification of specific inhibitors which selectively inhibit the mycobacterial aaRS (e.g., human control gene for an *M. tuberculosis* test gene; a bovine control gene for an *M. bovis* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a bovine control gene for an *M. tuberculosis* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous mycobacterial aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising an *M. tuberculosis* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous mycobacterial aaRS encoded by the test gene (or a step in the expression of the mycobacterial gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target mycobacterial aminoacyl-tRNA synthetase, such as a mycobacterial SerRS, could reduce the effectiveness of an inhibitor of aaRS activity. To test for mutations that confer resistance to an inhibitor (e.g., an inhibitor of SerRS activity, including such an inhibitor having antimicrobial activity) a variety of approaches can be used. Mutant mycobacterial aaRS genes can be obtained, for example, by isolation of a mutant gene, or by preparing an individual mutant gene or an expression library of mutant mycobacterial aaRS genes, such as a library of mutants of a mycobacterial SerRS gene. The mutant gene or gene library can be introduced into suitable host cells for screening for resistance to a compound.

An isolated mycobacterial tRNA synthetase gene, such as an *M. tuberculosis* SerRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli*, yeast, *Bacillus subtilis*, another mycobacterial species) aminoacyl-tRNA synthetase for the same amino acid, the mutant mycobacterial genes can be introduced into the wild-type host and the resulting cells can be exposed to drug to assess resistance.

In another embodiment, the procedures described above relating to tester strains are used in the method to identify mutants resistant to inhibitor. Introduction of the heterologous mycobacterial mutant aaRS gene(s) (i.e., mutant test gene(s)) into a host cell is carried out as described above for the production of tester strains. For example, the library can be introduced into a host cell having a defect in the endogenous gene encoding SerRS. The metG null strain of *E. coli* designated MN9261/pRMS615 is an example of the type of strain that can be constructed and used as a host for introduction of mutant mycobacterial aaRS gene(s) (in that case, MetRS genes; see Kim et al., *Proc. Natl. Acad. Sci. USA* 90: 10046–10050 (1993), describing a strain which carries a null allele of metG and a temperature sensitive maintenance plasmid, carrying a wild type metG allele (encoding *E. coli* MetRS) and having a temperature sensitive replicon which causes loss of the maintenance plasmid at the non-permissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., active recombinant *M. tuberculosis* MetRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the mycobacterial gene is indicated by growth at the non-permissive temperature at which the maintenance plasmid is lost. Cells which survive loss of the maintenance plasmid due to the presence of the complementing mutant gene are then challenged with inhibitor to assess resistance.

Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant mycobacterial aaRS gene, which confers resistance to an inhibitor upon a mycobacterial cell, can be isolated from the mycobacterium using nucleic acids of the present invention as probes. The cloned gene can then be introduced into a host cell as described for the production of tester strains. Tester cells comprising the mutant test gene which confers resistance, and complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The mycobacterial seryl-tRNA synthetase or stable subdomains of the protein can be used in a method to separate serine from a mixture of serine and other compounds such as other amino acids, or to specifically isolate L-serine from D-serine. The tRNA synthetase can be chemically attached to a solid support material packed in a column or other suitable container. Alternatively, a fusion protein such as a GST-Ser tRNA synthetase fusion or a His tail-Ser tRNA synthetase fusion permits attachment to a suitable solid support which binds the GST portion or His tail portion of the fusion protein, respectively. The mixture of serine and other compounds can be loaded onto the column under conditions in which serine binds to the tRNA synthetase enzyme, while other compounds present in the mixture flow through the column. In a later step, serine can be released from the enzyme by changing the conditions in the column, such as washing with a solution of high ionic strength to elute L-serine.

In a similar manner, the mycobacterial seryl-tRNA synthetase can be used in a method to isolate tRNA that specifically recognizes the tRNA synthetase.

The mycobacterial seryl-tRNA synthetase can be used in the quantitative determination of serine by its conversion to seryl hydroxamate. An example of an appropriate assay is illustrated by the following series of reactions:

serine+ATP→serine-AMP+PP$_i$ (in the presence of excess pyrophosphatase and ATP at pH 7.5, where pyrophosphatase catalyzes the conversion of the product inorganic pyrophospate (PP$_i$) to inorganic orthophospate (P$_i$); ATP is adenosine triphospate; AMP is adenosine monophosphate)

serine-AMP+NH$_2$OH→serine-NHOH+AMP (at pH 7.5)

serine-NHOH+FeCl$_3$→colored complex (at acidic pH)

The resulting colored complex can be quantitated by spectrophotometric measurements of absorbance at 540 nm, and compared with a standard curve made using known concentrations of serine. This assay is based on the reactions described by Stulberg and Novelli, *Methods in Enzymology* 5:703–707 (1962).

The mycobacterial seryl-tRNA synthetase can also be used for the quantitative determination of ATP. In the presence of excess serine, and in the presence of pyrophosphatase to convert the product PP$_i$ to P$_i$, the ATP will be quantitatively converted to AMP and inorganic pyrophosphate by the seryl-tRNA synthetase.

serine+ATP→seryl-AMP+PP$_i$ (in the presence of SerRS)

PP$_i$+H$_2$O→2P$_i$ (in the presence of pyrophosphatase)

P$_i$ can be quantitated by reaction with molybdate, measuring the absorbance at 580 nm and comparing to a standard curve made using known quantities of orthophosphate.

The present invention is more specifically illustrated in the following examples, which are not intended to be limiting in any way.

Example 1

Isolation of a Ser tRNA Synthetase Gene Fragment by PCR from *M. tuberculosis* Genomic DNA PCR was used to obtain a Ser tRNA synthetase gene fragment from *M. tuberculosis* genomic DNA (Erdman H37Rv; see Oatway, W. H., et al., *J. Infect. Dis.* 59:306–325 (1936)). The PCR primers were designed by aligning polypeptide sequences for different species of Ser tRNA synthetase (*Thermus thermophilus*, see Fujinaga, M, et al., *J. Mol. Biol.* 234:222–233 (1993); *E. coli*, see Härtlein, M. et al., *Nucleic Acids Res.* 15:1005–1017 (1987); *S. cerevisiae* (cytoplasmic), see Weygand-Durasevic, I., et al., *Nucleic Acids Res.* 15:1887–1904 (1987) and *Cricetelus griseus*, see Lunel, C., et al., *Nuc. Acids Res.* 20:2597 (1992)) using the PILEUP program (Needleman and Wunsch, J. *Mol. Biol.* 48:443–453 (1970)). A total of seven degenerate primers which are directed at two Ser tRNA synthetase sequence motifs were synthesized and used for PCR using a thermocycler (MJ Research, Inc., pTC-100). *M. tuberculosis* (Erdman H37Rv) genomic DNA (15 ng) was combined with 100 pmoles each of forward and reverse primer and mixed with Taq polymerase (1.5 units, Perkin-Elmer) in 50 ml of 10 mM Tris-HCl (tris(hydroxymethyl) aminomethane hydrochloride), pH 8.3, 1.5 mM MgCl$_2$, 50 mM KCl, 0.1 mg/ml gelatin, and 50 mM of each dNTP. The cycles for denaturation (95° C., 50"), annealing (50° C., 30") and extension (72° C., 60") were repeated 30 times. The PCR products were analyzed by gel electrophoresis: One combination of degenerate primers (Kiyo-142 (SEQ ID NO:1 and Kiyo-145 N (Ser145; SEQ ID NO:1) was successfully used to amplify a 212 basepair fragment. The PCR fragment was purified by Gene Clean (Bio 101) and was ligated to pT7Blue(R) (T-vector; Novagen) and the plasmid used to transform *E. coli* (NovaBlue from Novagen). The plasmid DNA was isolated using either Wizard miniprep kits (Promega) or Midi-prep kits (Qiagen). The Ser tRNA synthetase PCR fragments were sequenced using a Sequenase 7-Deaza-dGTP DNA sequencing kit (Version 2.0 T7 DNA Polymerase, USB). Standard protocols were used with the exception that 10% dimethylsulfoxide (DMSO) was included in all the reaction mixtures to facilitate the sequencing of DNA with a high G-C content.

Southern hybridization was carried out using standard protocols. The probe consisted of a 212 basepair fragment isolated from *M. tuberculosis* (strain Erdman H37Rv) genomic DNA using the probes Kiyo 142 and 145 N given in Table 1. The PCR-derived fragment was recovered from the derivative of pT7Blue(R) into which it had been cloned, by excision with NdeI and BamHI. The PCR fragment was radio-labeled with [$^{32}$P] using the Random Primer DNA Labeling Kit (Boehringer Mannheim) as described in the commercial protocol. One µg of genomic DNA from each of M. tuberculosis (Erdman H37Rv strain and H37Ra strain) and from E. coli was digested with EcoRI, separated by agarose gel electrophoresis, and transferred to a nylon membrane. The pre-hybridization was carried out by incubating the membranes in 50 ml of hybridization solution (5x Denhardt's solution, 5x SSC, 0.5% sodium dodecylsulfate (SDS), 4 mM EDTA and 100 µg/ml salmon sperm DNA) for a minimum of one hour at 65° C. The radiolabeled probe was denatured at 100° C. for 5 min and then a $1.5 \times 10^7$ cpm aliquot of probe was added to 50 ml of hybridization solution and incubated with the membrane overnight at 65° C. The membrane was washed a total of 3 times. The first wash was in 2x SSC (1x SSC is 150 mM NaCl, 15 mM Na-citrate, pH 7.0), 0.1% SDS for 5 min at 60° C.; the second wash was in 1x SSC, 0.1% SDS for 20 min at 65° C. The third wash was in 0.5x SSC, 0.1% SDS for 1 h at 65°C. The membrane was analyzed by autoradiography.

EXAMPLE 2

Screening of M. tuberculosis Genomic Library

The M. tuberculosis Ser tRNA synthetase PCR fragment was used as a probe to screen a λgt11 M. tuberculosis genomic library which was provided by Professor R. Young, Whitehead Institute, Cambridge, Mass. (Young, R. A., et al., Proc. Natl. Acad. Sci. USA 82:2583-2587 (1985)). The PCR fragment was recovered by a BamHI and NdeI digestion from the pT7Blue(R) derivative, purified from an agarose gel using a Geneclean kit (Bio 101), and 50 ng were radio-labelled using the Random Primer DNA Labeling Kit (Boehringer Mannheim) according to the commercial protocol. The labeled PCR fragment was purified using a Quick Spin column (Boehringer Mannheim). The typical yield was about $1 \times 10^8$ cpm/µg DNA.

The λgt11 library was spread on a plate (25×25 cm) to obtain about 100,000 plaques/plate. The plaques were transferred to duplicate Gene Screen, Hybridization Transfer nylon membranes (Dupont) and the DNA was denatured by soaking the membranes in 0.5N NaOH, 1.5M NaCl for 5 min followed by neutralization in 0.5M Tris, pH 7.5, 1.5M NaCl for 5 min. The membranes were washed in 2x SSC, air dried, and then baked at 80° C. for one hour. The pre-hybridization was carried out by incubating the membranes in 50 ml of hybridization solution (5x SSC, 5x Denhardt's solution, 0.5% SDS (sodium dodecyl sulfate), 4 mM EDTA (ethylenediamine tetraacetic acid), 100 µg/ml salmon sperm DNA) for a minimum of one hour at 65° C. The radiolabelled probe was denatured at 100° C. for 5 min and then a $1.5 \times 10^7$ cpm aliquot of probe was added to 50 ml of hybridization solution and incubated with the membrane overnight at 65° C. The membrane was washed a total of four times. The first wash was in 2x SSC, 0.1% SDS at 60° C. for 5 min; the second was in 1x SSC, 0.1% SDS at 65° C. for 20 min; the third was in 0.5x SSC, 0.1% SDS at 65° C. for 60 min, and the fourth was in 0.1X SSC, 0.1% SDS, 65° C. for 20 min. The membranes were analyzed by autoradiography.

Six positive plaques were selected from the duplicate membranes. The phage DNA was purified using the Wizard Lambda Preps DNA Purification System (Promega). DNA isolated from one of the positive plaques (Set 4) was digested with EcoRI, producing a 3.7 kb insert which was cloned into the EcoRI site of pBSKS+ (Stratagene) to yield pJZSer4, and used to transform E. coli (DH5α).

Plasmid pJZSer4 (in E. coli DH5α) was deposited in accordance with the provisions of the Budapest Treaty at the American Type Culture Collection (ATCC), 12301 Parklawn Drive, Rockville, Md. 20852, U.S.A. on May 16, 1996, and assigned Accession Number ATCC 98055.

EXAMPLE 3

Sequencing and Expression of M. tuberculosis Set tRNA Synthetase

The 3.7 kb fragment was sequenced in a sequential manner initially using primers based on the M. tuberculosis PCR fragment, and then sequencing was extended to both ends. Sequencing was performed using a Sequenase 7-Deaza-dGTP DNA sequencing kit (Version 2.0 T7 DNA polymerase, USB). Standard protocols were used with the exception that 10% dimethylsulfoxide (DMSO) was included in all the reaction mixtures to facilitate the sequencing of DNA with a high G-C content.

The nucleotide sequence determined for the M. tuberculosis seryl-tRNA synthetase gene is shown in SEQ ID NO:3. The 1,257 basepair sequence contains an open reading frame (ORF) which encodes a polypeptide of 419 amino acids (SEQ ID NO:4) translating from the GTG at position 1 of FIG. 1A. Random data base searches were carried out on the amino acid sequence of M. tuberculosis Ser tRNA synthetase (translating from the GTG at position 1 in SEQ ID NO:3) using the BLAST (Basic Local Alignment Search Tool) algorithm (See Altschul, S. F., et al., J. Mol. Biol. 215:403-410 (1990); Gish, W., and D. J. States, Nature Genetics, 3:266-272 (1993)) available from the National Center for Biotechnology Information in order to identify amino acid sequences in the database which are homologous to the sequence determined for M. tuberculosis Ser tRNA synthetase.

A further comparison of the sequence determined for M. tuberculosis Ser tRNA synthetase (translating from the GTG at position 1 in SEQ ID NO:3) with the SerRS sequences identified in these searches was performed using the multiple sequence alignment program from the DNA star package. In particular, percent similarity and percent divergence were determined using the Jotun-Hein method with the Structural residue weight table. When the predicted 419-amino acid sequence of M. tuberculosis Ser tRNA synthetase was compared with amino acid sequences identified as seryl-tRNA synthetase from Thermus thermophilus and Bacillus subtilis, the percent similarity was found to be 40.0% and 37.0%, respectively. Other sequences, such as those from E. coli, were even less related.

A fragment comprising the 1,257 basepair gene for M. tuberculosis Ser tRNA synthetase was cloned into four expression vectors: pGEX-4T-2 (Pharmacia), pGEX-KT (Pharmacia; see methods manual: GST Gene Fusion System published by Pharmacia (1993) for cloning vectors and methods of purifying glutathione-S-transferase fusion proteins expressed from vectors), pET-20b (Novagen) and pET-15b (Novagen). The ends of the gene were engineered by PCR using specifically designed PCR primers.

To construct a derivative of pGEX-4T-2, pJZSer4 DNA was used as template in a PCR amplification procedure that introduced altered ends onto the gene. The 5' PCR primer SEQ ID NO:5 (5' CGCGGATCCATGATCGACCTGAAGCTG 3') introduced a BamHI site and altered the GTG at position 1 (SEQ ID NO:3) to an ATG, while the 3' primer. (5' AAGGAATTCCGCGCTCGCGATCGCC 3') introduced an EcoRI restriction site downstream from the coding sequence. The PCR product, comprising the gene with ends as modified by PCR amplification using these primers, was digested with BamHI and EcoRI, and cloned into the BamHI and EcoRI sites of pGEX-4T-2. The resultant plasmid was designated pJZS201. In addition, the BamHI-EcoRI cleaved PCR product was used to clone the gene into the BamHI and EcoRI sites of pGEX-KT to yield pJZS220.

To construct an expression vector in pET-15b, a 5' PCR primer SEQ ID NO:7 (5' GGGAAATCCATATGATCGAC-CTGAAGCTG 3') which introduced an NdeI site and altered the GTG at position 1 SEQ ID NO:3 to an ATG, and a 3' primer SEQ ID NO:8 (5' CTTCGGATCCCGCTAAGC-GACCGGCTC 3') which included a BamHI site downstream from the coding region, were used to amplify the gene present in pJZSer4. The PCR product was digested with NdeI and BamHI, and cloned into the NdeI and BamHI sites of pET-15b. The resultant plasmid was designated pJZS301.

The NdeI and BamHI cleaved PCR product was also used to clone the gene into the NdeI and BamHI sites of pET-20b. The resulting plasmid was designated pJZS320. This construct is designed to express the protein shown in SEQ ID NO:4, starting translation from the ATG introduced by the 5' primer.

The pJZS201 and pJZS220 plasmids were each used to transform a DH5α strain of E. coli. The pJZS301 and pJZS320 plasmids, which require T7 RNA polymerase for expression of the cloned gene, were each used to transform BL21 (DE3) E. coli strain (Stratagene).

The transformed cells were grown 6–8 hours at 37° C. in 1.0 ml cultures of LB containing 60 μg/ml carbenicillin (Cb). The cultures were used to inoculate 5 ml LB (60 μg Cb/ml) cultures which were grown at 37° C. for 2–3 hours until the $A_{600}$ reached 0.6–0.8. Protein expression was induced by the addition of 0.1 mM of IPTG (isopropyl-β-D-thiogalactopyranoside) at 37° C. for a minimum of one hour. The cells were recovered by centrifugation, sonicated, and the crude cell extracts were analyzed by SDS-polyacrylamide gel electrophoresis on an 8% polyacrylamide gel. Coomassie staining revealed that the protein was expressed primarily in inclusion bodies from all of the vector constructions.

EXAMPLE 4

Purification of the M. tuberculosis GST-Ser tRNA Synthetase and His Tail-Ser tRNA Synthetase A 50 ml LB culture (60 μg Cb/ml) of E. coli harboring either the pJZS201 or pJZS301 plasmid was grown to an $A_{600}$ of 0.6. Protein expression was induced by the addition of IPTG to 0.1 mM, followed by continued growth at 37° C. for 1 hour. The cells were recovered by centrifugation in a Sorvall Super 21 (Dupont) and stored at −20° C. until purification.

The cells were suspended in 5 ml of 1x PBS and lysed by sonication at 75%/1 sec power using a Sonicator Ultrasonic Processor (Heat Systems) for about 10–20 sec until the solution cleared. A 50 μl aliquot of 20% Triton X-100 in 1x PBS was added followed by gentle mixing at 4° C. for 30 min. The lysis mixture was centrifuged at 12,000 g for 10 min at 4° C. to separate the inclusion bodies from the cell-free extract.

A batch purification of the GST-Ser tRNA synthetase was carried out using glutathione 4B agarose resin (14 mmol/ml, Sigma) which had been pre-equilibrated with 1x PBS. The cell-free extract was combined with 1.0 ml of the glutathione resin in an Eppendorf microfuge tube and gently rocked at 4° C. for 30 min. The tube was centrifuged briefly to precipitate the resin. The supernatant was discarded and the resin washed with 1x PBS. The protein was eluted in 10 mM reduced glutathione, 50 mM Tris, pH 8.0. The protein was identified by SDS-PAGE on an 8% polyacrylamide gel.

The His tail-Ser tRNA synthetase was expressed almost exclusively in inclusion bodies. The pellet from the cell lysis was recovered and initially washed in 20 mM Tris, pH 7.9, 50 mM NaCl, 5 mM imidazole. The protein was purified under denaturing conditions as described in the commercial protocol (Novagen). Briefly, the pellet was dissolved in binding buffer (20 mM Tris, pH 7.9, 50 mM NaCl, 5 mM imidazole, and 6M urea) and incubated on ice for 1 hour. The mixture was centrifuged for 20 min at 39,000 g at 4° C. The supernatant was loaded onto a 3.0 ml column filled with His-Bind Resin (Novagen) which had been pre-equilibrated with binding buffer. The column was washed with 10 volumes of binding buffer, followed by 6 volumes of wash buffer (binding buffer with the addition of 20 mM imidazole) and the protein was eluted in 30 mM Tris-HCl, pH 7.9, 500 mM NaCl, 500 mM imidazole, 6M urea. The protein was visualized by Coomassie blue staining subsequent to SDS-PAGE on an 8% polyacrylamide gel. The denatured protein was renatured by dialysis in 50 mM Tris, pH 8.0, 1 mM 2-mercaptoethanol and urea. Dialysis buffer changes involved successive decreases in urea, specifically 4M, 2M, and no urea, with three changes over 20 hours.

EXAMPLE 5

Assays for Aminoacylation Activity of M. tuberculosis GST-Ser tRNA Synthetase and His Tail-Ser tRNA Synthetase Aminoacylation reactions were carried out in 50 mM HEPES-KOH, pH 7.5, 10 mM 2-mercaptoethanol, 4 mM ATP, 10 mM $MgCl_2$, 20 μM serine plus [$^3$H] serine (Amersham) and 2 μM tRNA$^{Ser}$ transcript, using a procedure based on Martinis, S. A. and P. Schimmel, (Proc. Natl. Acad. Sci. USA 89:65–69 (1992); see also Sampson, J. and M. E. Saks Nucleic Acids Research 21:4467–4475 (1993)). Partially purified (by DEAE column) E. coli seryl-tRNA synthetase was assayed by the same procedure as a control. Prior to use, the tRNA$^{Ser}$ transcript was heated for 5 min at 80° C. and annealed on ice in the presence of 1 mM $MgCl_2$. The reaction was quenched by placing a 10 ml aliquot on a 2.3-cm Whatman 3MM filter pad, which was pre-soaked in 5% (v/v) trichloroacetic acid. The pads were slowly shaken on ice in 500 ml of of this wash solution with three changes for a total of 1 hour. The pads were incubated subsequently in 95% ethanol and ether and then dried under a heat lamp. To the filter pads were added 5 ml Betafluor (National Diagnostics) and the aminoacylated tRNA was quantitated by scintillation counting in a Packard 1600 TR scintillation counter.

EXAMPLE 6

Alternate Culture Conditions

A 200 ml LB culture (plus 60 μg/ml carbenicillin and 2% dextrose) of E. coli harboring the pJZS201 plasmid was grown to an $A_{600}$ of 2.0 at 37° C. A 10 ml aliquot of this culture was used to inoculate a fresh 100 ml culture (plus 60 μg/ml carbenicillin and 2% dextrose). Protein expression in both the original culture and 1:10 dilution was induced by the addition of IPTG to 0.1 mM, and the cultures were then maintained at 18° C. for an additional 3 days.

On each day a 1 ml aliquot of each culture was taken and the cell pellet was frozen. On the third day, the frozen cell pellets were resuspended in 100 µl 1X PBS containing 1 µl AMSF (protease inhibitor), lysed by sonication, and spun for 10 minutes in a microfuge. The supernatants were combined with loading buffer and fractionated on 8% SDS-polyacrylamide gels. Analysis of the gel did not clearly show an increase in the amount of GST-Ser tRNA synthetase protein in the soluble fraction; however, the procedure led to an observable increase in the amount of protein in the soluble fraction in the case of a GST-fusion protein comprising *M. tuberculosis* leucyl-tRNA synthetase. Therefore, the remaining *E. coli* cells harboring the pJZS201 were recovered by centrifugation in a Sorvall Super 21 (Dupont) and stored at −20° C. These frozen cell pellets can be used to purify GST-Ser tRNA synthetase protein as described in Example 4, for example.

Related Mycobacterial Aminoacyl tRNA Synthetases and Tester Strains

In addition to the gene encoding seryl-tRNA synthetase described herein, genes encoding methionyl-, leucyl-, isoleucyl-, and tyrosyl-tRNA synthetases from *M. tuberculosis* have been isolated and sequenced as described in U.S. Ser. No. 08/305,766 (Attorney Docket No. CPI94-05), U.S. Ser. No. 08/305,171 (Attorney Docket No. CPI94-06), U.S. Ser. No. 08/305,765 (Attorney Docket No. CPI94-08) and U.S. Ser. No. 08/305,181 (Attorney Docket No. CPI94-20), respectively, filed concurrently herewith, and the teachings of which are each hereby incorporated by reference in their entirety. These isolated genes are representatives of a broader class of mycobacterial aminoacyl-tRNA synthetase genes, including synthetase genes encoding enzymes specific for each amino acid and derived from various species of mycobacteria, each of which gene can be used to express mycobacterial aminoacyl-tRNA synthetase protein, with utilities corresponding to those described herein, and which can be used in the production of tester strains comprising recombinant mycobacterial aminoacyl-tRNA synthetase genes by methods analogous to those described herein. The approaches described herein, including, but not limited to, the approaches to isolate and manipulate the methionyl-, leucyl-, seryl-, isoleucyl- and tyrosyl-tRNA synthetase genes of *M. tuberculosis*, to construct vectors and host strains, to produce and use the enzymes, to produce antibodies, etc., can be applied to other aminoacyl-tRNA synthetases of the genus Mycobacterium.

TABLE 1

| Species | Degenerate PCR Primers Polypeptide Sequence (N- → C-terminal)/Degenerate Primer | | | | | | | | | |
|---|---|---|---|---|---|---|---|---|---|---|
| Ec-S (SEQ ID NO: 11) | K | T | Y | D | L | E | V | W | I | P |
| Sc-S (SEQ ID NO: 12) | K | k | Y | D | L | E | a | W | f | P |
| Cg-S (SEQ ID NO: 13) | K | k | l | D | L | E | a | w | f | P |
| Kiyo-142 (5'→3') | AAR | ACI | TAY | GAY | CTI | GAR | GTI | TGG | ATH | CC (SEQ ID NO: 1) |
| Ec-S (SEQ ID NO: 14) | E | N | Y | Q | Q | A | D | G | | |
| Sc-S (SEQ ID NO: 15) | E | N | Y | Q | t | e | D | G | | |
| Cg-S (SEQ ID NO: 16) | E | N | Y | Q | t | e | k | G | | |
| (5'→3') | GAR | AAY | TAY | CAR | CAR | GCI | GAY | GG (SEQ ID NO: 9) | | |
| Kiyo-145 (3'→5') | CTY | TTR | ATR | GTY | GTY | CGI | CTR | CC (SEQ ID NO: 10) | | |
| Kiyo-145 N (3'→5') | CTY | TTR | ATR | GTY | GTY | CGN | CTR | CC (SEQ ID NO: 2) | | |

Degenerate primers were specifically designed to amplify aminoacyl-tRNA synthetase gene fragments by PCR from *M. tuberculosis* or *M. kansasii* genomic DNA, or from the DNA of other organisms. Lower case amino acid abbreviations indicate amino acid residues whose codons are not complementary to the corresponding degenerate primer.

Abbreviations

Amino acids:

Standard single letter amino acid codes are used.

Bases:

I—inosine

R—A,G

Y—T,C

M—A,C

W—A,T

S—G,C

H—A,T,C

N—A,T,C,G

Ec—*E. coli*

SC—*S. cerevisiae*

Cg—*Cricetelus griseus*

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. An isolated, recombinant nucleic acid which encodes a seryl-tRNA synthetase of the genus Mycobacterium.

2. An essentially pure nucleic acid which hybridizes under stringent temperature conditions to DNA having the sequence in SEQ ID NO:3 and encodes a seryl-tRNA synthetase of the genus Mycobacterium.

3. An isolated, recombinant nucleic acid which encodes a seryl-tRNA synthetase of *Mycobacterium tuberculosis*.

4. An essentially pure nucleic acid of claim 2 wherein the seryl-tRNA synthetase is a seryl-tRNA synthetase of *Mycobacterium tuberculosis*.

5. An essentially pure nucleic acid which encodes the amino acid sequence in SEQ ID NO:4.

6. A recombinant nucleic acid vector comprising a nucleic acid which encodes a mycobacterial seryl-tRNA synthetase and which hybridizes under stringent temperature conditions to DNA having the sequence in SEQ ID NO:3.

7. A recombinant DNA vector which contains DNA which encodes a mycobacterial seryl-tRNA synthetase.

8. A recombinant nucleic acid vector of claim 6 wherein the seryl-tRNA synthetase is a seryl-tRNA synthetase of *Mycobacterium tuberculosis*.

9. A recombinant DNA vector comprising DNA which encodes a seryl-tRNA synthetase of *Mycobacterium tuberculosis*.

10. A host cell which contains a recombinant mycobacterial seryl-tRNA synthetase gene which can express a mycobacterial seryl-tRNA synthetase.

11. A host cell of claim 10 in which the recombinant mycobacterial seryl-tRNA synthetase gene can express a *Mycobacterium tuberculosis* seryl-tRNA synthetase.

12. An expression vector comprising a nucleic acid encoding a fusion protein comprising a mycobacterial seryl-tRNA synthetase, wherein said nucleic acid comprises a coding sequence for mycobacterial seryl-tRNA synthetase, wherein the coding sequence is under the control of transcription signals and is linked to appropriate translation signals for expression in a suitable host cell.

13. A method for producing active mycobacterial seryl-tRNA synthetase comprising the following steps:

a) constructing a recombinant nucleic acid vector comprising a coding sequence for mycobacterial seryl-tRNA synthetase wherein the coding sequence is under the control of transcription signals and is linked to appropriate translation signals;

b) introducing the vector into suitable host cells which support the replication of the vector; and c) maintaining the host cells under conditions in which mycobacterial seryl-tRNA synthetase is expressed.

14. An isolated nucleic acid comprising a nucleic acid having a sequence complementary to a DNA strand having the sequence in SEQ ID NO:3 or to an RNA counterpart of the sequence in SEQ ID NO:3.

15. A method for producing a mycobacterial seryl-tRNA synthetase comprising maintaining a host cell comprising a recombinant nucleic acid encoding a mycobacterial seryl-tRNA synthetase under conditions suitable for expression of the nucleic acid, whereby a mycobacterial seryl-tRNA synthetase is expressed and thereby produced.

16. An isolated nucleic acid, wherein said nucleic acid encodes a protein comprising a seryl-tRNA synthetase which is encoded by pJZSer4 as deposited under ATCC Accession No. 98055 or a derivative of pJZSer4 in which G at position 1 is altered to A.

17. The isolated nucleic acid of claim 16, wherein the protein is a fusion protein.

18. The isolated nucleic acid of claim 16, which is essentially pure.

19. A host cell comprising a recombinant nucleic acid, wherein said nucleic acid encodes a protein comprising a seryl-tRNA synthetase which is encoded by pJZSer4 as deposited under ATCC Accession No. 98055 or a derivative of pJZSer4 in which G at position 1 is altered to A.

* * * * *